United States Patent [19]
Farr et al.

[11] Patent Number: 5,262,425
[45] Date of Patent: Nov. 16, 1993

[54] ALPHA-MANNOSIDASE INHIBITORS

[75] Inventors: Robert A. Farr, Loveland; Mohinder S. Kang, Cincinnati; Norton P. Peet, Cincinnati; Sai P. Sunkara, Cincinnati, all of Ohio

[73] Assignee: Merrell Dow Pharmaceuticals Inc., Cincinnati, Ohio

[21] Appl. No.: 893,171

[22] Filed: Jun. 3, 1992

Related U.S. Application Data

[63] Continuation-in-part of Ser. No. 761,579, Sep. 18, 1991, abandoned.

[51] Int. Cl.$^5$ .............................................. A61K 31/44
[52] U.S. Cl. .................................. 514/299; 546/112; 536/27.1; 514/43
[58] Field of Search .................. 546/112; 514/299, 43; 536/23

[56] References Cited

U.S. PATENT DOCUMENTS 4,031,102  6/1977  Curran et al. ...................... 546/112

FOREIGN PATENT DOCUMENTS 2088860  6/1982  United Kingdom .

Primary Examiner—Thurman K. Page
Assistant Examiner—G. Kishore

[57] ABSTRACT

[4S-(4α,4aβ,5β,6α,7α,7aα)]-Octahydro-1H-1-pyrindine-4,5,6,7-tetrols and [4R-(4α,4aα,5α,6β,7β,7aβ)]-octahydro-1H-1-pyrindine-4,5,6,7-tetrols are useful as inhibitors of alpha-mannosidase and are useful immunostimulants, chemoprotective and radioprotective agents and antimetastatic agents.

8 Claims, No Drawings

ALPHA-MANNOSIDASE INHIBITORS

BACKGROUND OF THE INVENTION

This application is a continuation-in-part of U.S. application Ser. No. 07/761,579 filed Sep. 18, 1991 abandoned.

Most human cancers are treated by the use of radio and/or chemotherapeutic agents. There are mainly two problems associated with the use of such techniques in the treatment of cancer, namely, adverse side effects and resistance to the use of cytotoxic chemical agents. These phenomena limit the usefulness of such therapies. Regulation of the growth and differentiation of hematopoietic progenitor cells is under the control of several growth factors. It is well known that immunomodulators such as interleukins, granulocyte-macrophage colony stimulating factors, tumor necrosis factor and bacterial lipopolysaccharides, due to their ability to enhance hematopoietic and immune functions, confer radio and chemoprotection. Recently, swainsonine has been demonstrated to mimic growth promoting activities of various hematopoietic growth factors and offer protection from radiation and cytotoxic chemotherapy. S. L. White et al., *Cancer Communications*, 3(3), 83–91, 1991.

Swainsonine, a plant alkaloid initially isolated from Australian plant Swainsona canescens, has been demonstrated to be a potent and specific inhibitor of golgi alpha-mannosidase II, a glycoprotein processing enzyme. (Colegate et al., *Aust. J. Chem.* 32: 2257–2264, 1979.) Swainsonine has also been shown to have many other biological effects including inhibition of tumor growth, metastasis, augumentation of host immune effector mechanisms and activation of protein kinase-C. (C. Kino et al., *J. Antibiotics*, 38(7), 926–940, 1985.) Although it is not clear by which mechanism(s) swainsonine offers radio/chemoprotection, inhibitors of alpha-mannosidase and analogs of swainsonine are expected to be useful as radio/chemoprotective agents.

Applicants have now discovered a new class of alpha-mannosidase inhibitors which are useful as immunomodulators, chemo- and radioprotective agents and as antimetastatic agents.

SUMMARY OF THE INVENTION

This invention relates to novel alpha-mannosidase inhibitors of formula 1

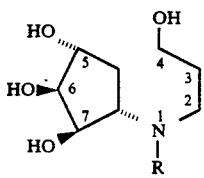

wherein

R is a hydrogen, a ($C_1$–$C_6$)alkyl optionally substituted with one or two hydroxy groups, a glycosyl group, or a group of the formula —$(CH_2)_n$—Ar wherein n is an integer of from 1 to 4 and Ar is a phenyl group optionally substituted with one or two groups selected from ($C_1$–$C_4$)alkyl, ($C_1$–$C_4$)alkoxy, F, Cl, Br, I, amino, mono($C_1$–$C_4$)alkylamino, or di($C_1$–$C_4$)alkylamino, or a pharmaceutically acceptable salt thereof which are useful as immunostimulants, chemoprotective agents, radioprotective agents and as antimetastatic agents.

DETAILED DESCRIPTION OF THE INVENTION

The usual stereochemical conventions are used throughout to denote the relative spatial orientation of groups attached to the rings. Thus, a solid line diverging from the point of attachment to a ring indicates that the attached group is in the beta-configuration, that is, the group is above the plane of the ring. Likewise, a dotted line indicates that the attached group is in the alpha-configuration, that is, the group is below the plane of the ring. Attachment of a group to a ring by a normal, not divergent or dotted, line indicates that the spatial orientation can be either alpha or beta.

The $C_1$–$C_6$)alkyl groups of this invention can be straight chained, branched chain or cyclic. Examples of such alkyl groups are methyl, ethyl, n-propyl, isopropyl, n-butyl, isobutyl, tert-butyl, n-pentyl, isopentyl, cyclopentyl, n-hexyl, and cyclohexyl.

In those alkyl groups substituted with two hydroxy groups, the hydroxy groups will not be bonded to the same carbon atom. Further, the hydroxy group will not be bonded to the carbon atom which is bonded to the amino nitrogen atom.

The glycosyl groups of this invention can be mono-, di- or trisaccharide moieties. The glycosyl group can be attached to the amino nitrogen atom through either an exocyclic or ring carbon atom of the glycosyl pentose or hexose ring thereby forming a variety of possible positional isomers for each individual glycosyl group. Also similar or dissimilar pentose or hexose moieties may be linked to each other through a glycosidic oxygen bridge wherein the bridging oxygen atom is attached to an exocyclic and/or endocyclic carbon atom of the pentose or hexose moiety of which the glycosyl radical is comprised; again all positional isomers are contemplated as within the scope of this invention.

Exemplary of glycosyl radicals contemplated are such monosaccharides as glucosyl, galactosyl, mannosyl, fucosyl, ribosyl, 2-deoxyglucosyl, 3-O-methylglucosyl, xylosyl, and arabinosyl, disaccharides as alpha- and beta-cellobiosyl, isomaltosyl, trehalosyl, and maltosyl, and such trisaccharides as maltotriosyl, and cellotriosyl. Particularly preferred are the compounds wherein R is mannosyl.

Acid addition salts with pharmaceutically acceptable acids referred to above are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

Of those compounds of formula 1, those compounds wherein R is a methyl or ethyl, benzyl, a 1,3-dihydroxyprop-2-yl, 2-hydroxypropyl and mannosyl are preferred. Also preferred are those compounds of formula 1 whererin the 4-hydroxy group is in the alpha-configuration.

The compounds of formula 1 can be prepared by techniques and procedures well known and appreciated by one of ordinary skill in the art. A general synthetic scheme for preparing the compounds of this invention is set forth in Scheme A. In Scheme A, all substitutents are as previously defined unless otherwise indicated.

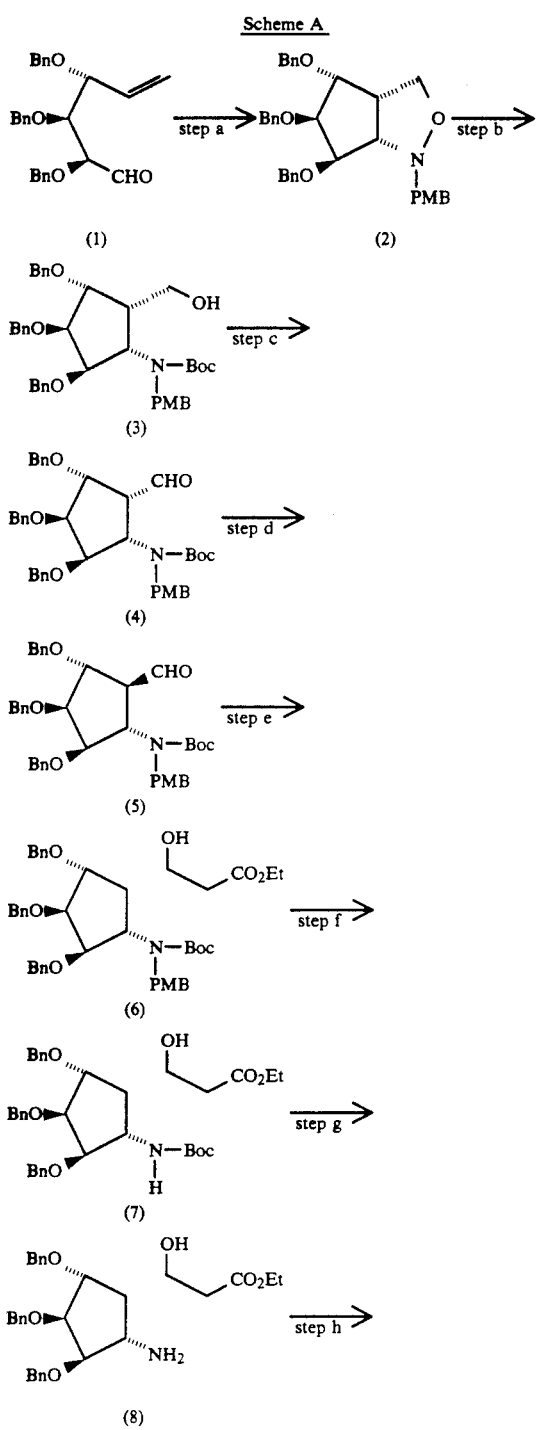

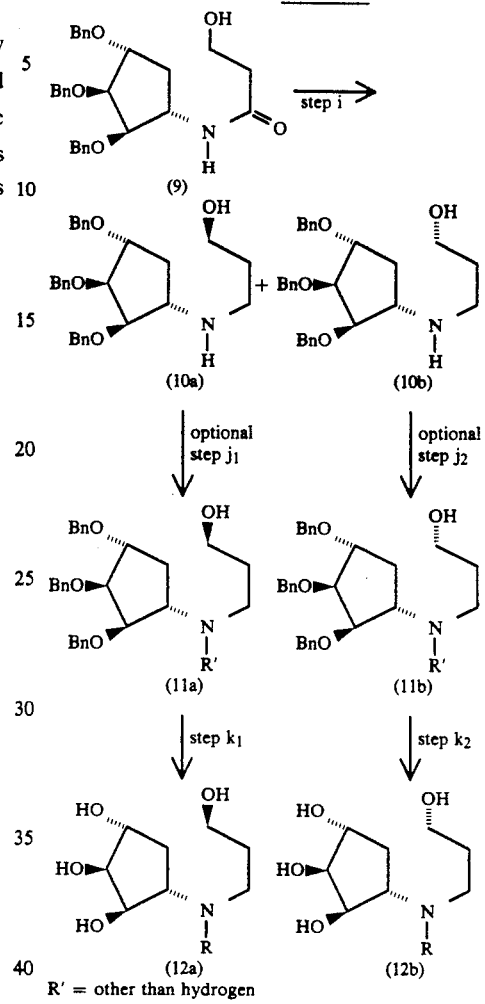

R' = other than hydrogen

Scheme A provides a general synthetic procedure for preparing compounds of formula 1.

In step a, 2,3,4-tris(phenylmethoxy)-5,6-dideoxy-D-lyxo-hex-5-enose (1) is reacted with 4-methoxybenzylhydroxylamine to give [3aS-(3aα,4β,5α,6α,6aα)]-hexahydro-1-[(4-methoxyphenyl)methyl]-4,5,6-tris(phenylmethoxy)-1H-cyclopent[c]isoxazole (2).

For example, 2,3,4-tris(phenylmethoxy)-D-lyxo-hex-5-enose (1) is contacted with an slight molar excess of 4-methoxybenzylhydroxylamine. The reactants are typically contacted in a suitable protic organic solvent such as methanol. The reactants are typically contacted for a period of time ranging from 5-24 hours at a temperature range of from room temperature to reflux. [3aS-(3aα,4β,5α,6α,6aα)]-Hexahydro-1-[(4-methoxyphenyl)methyl]-4,5,6-tris(phenylmethoxy)-1H-cyclopent[c]isoxazole (2) is recovered from the reaction zone by basification followed by extractive methods as is known in the art. It may be purified by silica gel chromatography.

In step b, [3aS-(3aα,4β,5α,6α,6aα)]-hexahydro-1-[(4-methoxyphenyl)methyl]-4,5,6-tris(phenylmethoxy)-1H-cyclopent[c]isoxazole (2) is reduced to give [1S-(1α,2α,-3α,4β,5β)]-[2-(hydroxymethyl)-3,4,5-(phenylmethoxy)-cyclopentyl][(4-methoxyphenyl)methyl]amine followed by acylation with di-tert-butyl dicarbonate to give [1S-(1α,2α,3α,4β,5β)]-[2-(hydroxymethyl)-3,4,5-(phenylmethoxy)cyclopentyl][(4-methoxyphenyl)methyl]carbamic acid, 1,1-dimethylethyl ester (3).

The reduction can be accomplished by any means known to those skilled in the art for reduction of the oxygen-nitrogen bond provided that the reaction conditions do not substantially affect the relative stereochemistry of the groups.

For example, [3aS-(3aα,4β,5α,6α,6aα)]-hexahydro-1-[(4-methoxyphenyl)methyl]-4,5,6-tris(phenylmethoxy)-1H-cyclopent[c]isoxazole of structure (2) is contacted with a molar excess of activated zinc dust. The reactants are typically contacted in a suitable acid medium such as acetic acid. The reactants are typically stirred together for a period of time ranging from 1-5 hours at a temperature range of from room temperature to reflux. The intermediate [1S-(1α,2α,3α,4β,5β)]-[2-(hydroxymethyl)-3,4,5-(phenylmethoxy)cyclopentyl][(4-methoxyphenyl)methyl]amine is recovered from the reaction zone by extractive methods as is known in the art.

The intermediate [1S-(1α,2α,3α,4β,5β)]-[2-(hydroxymethyl)-3,4,5-(phenylmethoxy)cyclopentyl][(4-methoxyphenyl)methyl]amine is contacted with a molar excess of di-tert-butyl dicarbonate. The reactants are typically contacted in a suitable aprotic organic solvent such as tetrahydrofuran. The reactants are typically stirred together for a period of time ranging from 2-24 hours at a temperature range of from room temperature to reflux. [1S-1α,2α,3α,4β,5β)]-[2-(Hydroxymethyl)-3,4,5-(phenylmethoxy)cyclopentyl][(4-methoxyphenyl)methyl]carbamic acid, 1,1-dimethylethyl ester (3) is recovered from the reaction zone by extractive methods as is known in the art. It may be purified by silica gel chromatography.

In step c, [1S-(1α,2α,3α,4β,5β)]-[2-(hydroxymethyl)-3,4,5-(phenylmethoxy)cyclopentyl][(4-methoxyphenyl)methyl]carbamic acid, 1,1-dimethylethyl ester (3) is oxidized to give [1S-(1α,2α,3α,4β,5β)]-[2-formyl-3,4,5-tris(phenylmethoxy)cyclopentyl][(4-methoxyphenyl)methyl]carbamic acid, 1,1-dimethylethyl ester (4).

The oxidation can be accomplished by any means known to those skilled in the art for oxidation of the hydroxymethyl group provided that the reaction conditions do not substantially affect the relative stereochemistry of the other positions, or cause one of the substituents on the cyclopentane ring to be lost in a β-elimination process.

For example, [1S-(1α,2α,3α,4β,5β)]-[2-(hydroxymethyl)-3,4,5-(phenylmethoxy)cyclopentyl][(4-methoxyphenyl)methyl]carbamic acid, 1,1-dimethylethyl ester (3) is contacted with 2 molar equivalents of Dess-Martin periodinane. The reactants are typically contacted in a suitable aprotic organic solvent such as methylene chloride. The reactants are typically stirred together for a period of time ranging from 5 minutes to 2 hours and at a temperature range of from 0° C. to room temperature. [1S-(1α,2α,3α,4β,5β)]-[2-Formyl-3,4,5-tris(phenylmethoxy)cyclopentyl][(4-methoxyphenyl)methyl]carbamic acid, 1,1-dimethylethyl ester (4) is recovered from the reaction zone by extractive methods as is known in the art.

Alternatively, [1S-(1α,2α,3α,4β,5β)]-[2-(hydroxymethyl)-3,4,5-(phenylmethoxy)cyclopentyl][(4-methoxyphenyl)methyl]carbamic acid, 1,1-dimethylethyl ester (3) is contacted with a molar excess of dicyclohexylcarbodiimide, molar excess of dimethylsulfoxide, a slight molar excess of pyridine and a molar deficiency of an acid such as trifluoroacetic acid. The reactants are typically contacted in a suitable aprotic organic solvent such as toluene. The reactants are typically stirred together for a period of time ranging from 1-24 hours and at a temperature range of from 10° C. to room temperature. [1S-(1α,2α,3α,4β,5β)]-[2-Formyl-3,4,5-tris(phenylmethoxy)cyclopentyl][(4-methoxyphenyl)methyl]carbamic acid, 1,1-dimethylethyl ester (4) is recovered from the reaction zone by extractive methods as is known in the art.

In step d, the alpha carboxaldehyde of [1S-(1α,2α,3α,4β,5β)]-[2-formyl-3,4,5-tris(phenylmethoxy)cyclopentyl][(4-methoxyphenyl)methyl]carbamic acid, 1,1-dimethylethyl ester (4) is inverted to the beta position to give [1S-(1α,2β,3α,4β,5β)]-[2-formyl-3,4,5-tris(phenylmethoxy)cyclopentyl][(4-methoxyphenyl)methyl]-carbamic acid, 1,1-dimethylethyl ester (5).

For example, [1S-(1α,2α,3α,4β,5β)]-[2-tris(phenylmethoxy)cyclopentyl][(4-methoxyphenyl)methyl]carbamic acid, 1,1-dimethylethyl ester (4) is contacted with less than a molar excess of a non-nucleophilic base such as 1,8-diazabicyclo[5.4.0]undec-7-ene. The reactants are typically contacted in a suitable aprotic organic solvent such as methylene chloride. The reactants are typically stirred together for a period of time ranging from 1-5 hours and at a temperature range of from −78° C. to −40° C. [1S-(1α,2β,3α,4β,5β)]-[2-Formyl-3,4,5-tris(phenylmethoxy)-cyclopentyl][(4-methoxyphenyl)methyl]carbamic acid, 1,1-dimethylethyl ester (5) is recovered from the reaction zone by acidification followed by extractive methods as is known in the art.

Alternatively, the alpha carboxaldehyde of [1S-(1α,2α,3α,4β,5β)]-[2-formyl-3,4,5-tris(phenylmethoxy)cyclopentyl][(4-methoxyphenyl)methyl]carbamic acid, 1,1-dimethylethyl ester (4) is inverted to the beta position to give [1S-(1α,2β,3α,4β,5β)]-[2-formyl-3,4,5-tris(phenylmethoxy)cyclopentyl][(4-methoxyphenyl)methyl]carbamic acid, 1,1-dimethylethyl ester (5) merely by silica gel chromatography.

In step e, [1S-(1α,2β,3α,4β,5β)]-[2-formyl-3,4,5-tris(phenylmethoxy)cyclopentyl][(4-methoxyphenyl)methyl]carbamic acid, 1,1-dimethylethyl ester (5) is alkylated with ethyl acetate to give [1R,2S,3R,4S,5R]-2-[[(1,1-dimethylethoxy)carbonyl][(4-methoxyphenyl)methyl]amino]-β-hydroxy-3,4,5-tris(phenylmethoxy)cyclopentanepropanoic acid, ethyl ester (6).

For example, a molar excess of ethyl acetate is first contacted with a suitable non-nucleophilic base such as lithium hexamethyldisilazide. The reactants are typically contacted in a suitable aprotic organic solvent such as tetrahydrofuran. The reactants are typically stirred together for a period of time ranging from 5-60 minutes and at a temperature range of from −78° C. to −40° C.

A solution of [1S-(1α,2β,3α,4β,5β)]-[2-formyl-3,4,5-tris(phenylmethoxy)cyclopentyl][(4-methoxyphenyl)methyl]carbamic acid, 1,1-dimethylethyl ester (5) in a suitable aprotic organic solvent such as tetrahydrofuran is then added. The reactants are typically stirred together for a period of time ranging from 15 minutes to 1 hour and at a temperature range of from −78° C. to −40° C. [1R,2S,3R,4S,5R]-2-[[(1,1-Dimethylethoxy)carbonyl][(4-methoxyphenyl)methyl]amino]-β-hydroxy-3,4,5-tris(phenylmethoxy)cyclopentanepropanoic acid, ethyl ester (6) is recovered from the reaction zone by acidification followed by extractive methods as is known in the art. It may be purified by silica gel chromatography.

In step f, the N-p-methoxybenzyl group of [1R,2S,3R,4S,5R]-2-[[(1,1-dimethylethoxy)carbonyl][(4-methoxyphenyl)methyl]amino]-β-hydroxy-3,4,5-tris(phenylmethoxy)cyclopentanepropanoic acid, ethyl ester of structure (6) is removed to give [1R,2S,3R,4S,5R]-β-hydroxy-2-[[(1,1-dimethylethoxy)carbonyl]amino]-3,4,5-tris(phenylmethoxy)cyclopentanepropanoic acid, ethyl ester (7).

For example, [1R,2S,3R,4S,5R]-2-[[(1,1-dimethylethoxy)carbonyl][(4-methoxyphenyl)methyl]amino]-β-hydroxy-3,4,5-tris(phenylmethoxy)cyclopentanepropanoic acid, ethyl ester of structure (6) is contacted with 3 molar equivalents of ceric ammonium nitrate. The reactants are typically contacted in a suitable protic solvent mixture such as acetonitrile/water. The reactants are typically stirred together for a period of 15 minutes to 3 hours and at a temperature range of from 0° C. to room temperature. 1R,2S,3R,4S,5R]-2-[[(1,1-dimethylethoxy)carbonyl]amino]-β-hydroxy-3,4,5-tris(phenylmethoxy)cyclopentanepropanoic acid, ethyl ester (7) is recovered from the reaction zone by extractive methods as is known in the art. It may be purified by distillation and/or recrystallization.

In step g, the N-tert-butylcarboxy group of [1R,2S,3R,4S,5R]-2-[[(1,1-dimethylethoxy)carbonyl]amino]-β-hydroxy-3,4,5-tris(phenylmethoxy)cyclopentanepropanoic acid, ethyl ester (7) is removed to give [1R,2S,3R,4S,5R]-2-amino-β-hydroxy-3,4,5-tris(phenylmethoxy)cyclopentanepropanoic acid, ethyl ester (8).

For example, [1R,2S,3R,4S,5R]-2-[[(1,1-dimethylethoxy)carbonyl]amino]-β-hydroxy-3,4,5-tris(phenylmethoxy)cyclopentanepropanoic acid, ethyl ester (7) is contacted with a molar excess of hydrogen chloride gas. The reactants are typically contacted in a suitable aprotic organic solvent such as ethyl ether. The reactants are typically stirred together for a period of time ranging from 25-75 minutes and at a temperature range of from 0° C. to room temperature. [1R,2S,3R,4S,5R]-2-amino-β-Hydroxy-3,4,5-tris(phenylmethoxy)cyclopentanepropanoic acid, ethyl ester (8) as a mixture of epimers is recovered from the reaction zone by basification followed by extractive methods as is known in the art.

In step h, [1R,2S,3R,4S,5R]-2-amino-β-3,4,5-tris(phenylmethoxy)-cyclopentanepropanoic acid, ethyl ester (8) is cyclized to give [4aR,5R,6S,7R,7aS]-octahydro-4-hydroxy-5,6,7-tris(phenylmethoxy)-2H-1-pyrindin-2-one (9).

For example, [1R,2S,3R,4S,5R]-2-amino-β-hydroxy-3,4,5-tris(phenylmethoxy)cyclopentanepropanoic acid, ethyl ester (8) is contacted with a catalytic amount of a suitable base such as sodium methoxide in methanol. The reactants are tyically stirred together for a period of time ranging from 15 minutes to 5 hours and at a temperature range of from room temperature to reflux. [4aR,5R,6S,7R,7aS]-Octahydro-4-hydroxy-5,6,7-tris(phenylmethoxy)-2H-1-pyrindin-2-one (9) is recovered from the reaction zone by extractive methods as is known in the art.

In step i, [4aR,5R,6S,7R,7aS]-octahydro-4-hydroxy-5,6,7-tris(phenylmethoxy)-2H-1-pyrindin-2-one (9) is reduced to give [4S-(4α,4aβ,5β,6α,7α,7aβ)]-octahydro-5,6,7-tris(phenylmethoxy)-1H-1-pyrindin-4-ol of structure (10a) and [4R-(4α,4aα,5α,6β,7β,7aβ)]-octahydro-5,6,7-tris(phenylmethoxy)-1H-1-pyrindin-4-ol (10b).

For example, [4aR,5R,6S,7R,7aS]-octahydro-4-hydroxy-5,6,7-tris(phenylmethoxy)-2H-1-pyrindin-2-one (9) is contacted with a slight molar excess of a suitable reducing agent such as lithium aluminum hydride. The reactants are typically contacted in a suitable aprotic organic solvent such as tetrahydrofuran. The reactants are typically stirred together for a period of time ranging from 1-5 hours and at a temperature range of from room temperature to reflux. [4S-(4α,4aβ,5β,6α,7α,7aα)]-octahydro-5,6,7-tris(phenylmethoxy)-1H-1-pyrindin-4-ol of structure (10a) and [4R-(4α,4aα,5α,6β,7β,7aβ)]-octahydro-5,6,7-tris(phenylmethoxy)-1H-1-pyrindin-4-ol (10b) are recovered from the reaction zone by extractive methods as is known in the art and separated by silica gel chromatography.

In optional step j₁, [4S-(4α,4aβ,5β,6α,7α,7aα)]-octahydro-5,6,7-tris(phenylmethoxy)-1H-1-pyrindin-4-ol of structure (10a) is N-alkylated to give the appropriate [4S-(4α,4aβ,5β,6α,7α,7aα)]-octahydro-1-alkyl-5,6,7-tris(phenylmethoxy)-1H-1-pyrindin-4-ol of structure (11a).

For example, reductive amination of [4S-(4α,4aβ,5β,6α,7α,7aα)]-octahydro-5,6,7-tris(phenylmethoxy)-1H-1-pyrindin-4-ol (10a) with an equimolar amount of the appropriate aldehyde and an equimolar amount of sodium cyanoborohydride as is known in the art gives the appropriate [4S-(4α,4aβ,5β,6α,7α,7aα)]-octahydro-1-alkyl-5,6,7-tris(phenylmethoxy)-1H-1-pyrindin-4-ol of structure (11a).

Alternatively, alkylation of [4S-(4α,4aβ,5β,6α,7α,7aα)]-octahydro-5,6,7-tris(phenylmethoxy)-1H-1-pyrindin-4-ol (10a) with an equimolar amount of an apropriate alkyl halide and an equimolar amount of a suitable base such as potassium carbonate as is known in the art gives the appropriate [4S-(4α,4aβ,5β,6α,7α,7aα)]octahydro-1-alkyl-5,6,7-tris(phenylmethoxy)-1H-1-pyrindin-4-ol of structure (11a).

In optional step j₂,[4R-(4α,4aα,5α,6β,7β,7aβ)]octahydro-5,6,7-tris(phenylmethoxy)-1H-1-pyrindin-4-ol (10b) is N-alkylated to give [4R-(4α,4aα,5α,6β,7β,7aβ)-]octahydro-1-alkyl-5,6,7-tris(phenylmethoxy)-1H-1-pyrindin-4-ol of structure (11b) as described in optional step j₁.

In step k₁, [4S-(4α,4aβ,5β,6α,7α,7aα)]-octahydro-5,6,7-tris(phenylmethoxy)-1H-1-pyrindin-4-ol (10a) or the appropriate [4S-(4α,4aβ,5β,6α,7α,7aα)]-octahydro-1-alkyl-5,6,7-tris(phenylmethoxy)-1H-1-pyrindin-4-ol of structure (11a) is deprotected to give the appropriate [4S-(4α,4aβ,5β,6α,7α,7aα)]-octahydro-1H-1-pyrindine-4,5,6,7-tetrol of structure (12a).

For example, [4S-(4α,4aβ,5β,6α,7α,7aα)]-octahydro-5,6,7-tris(phenylmethoxy)-1H-1-pyrindin-4-ol (10a) or [4S-(4α,4aβ,5β,6α,7α,7aα)]-octahydro-1-alkyl-5,6,7-tris(phenylmethoxy)-1H-1-pyrindin-4-ol of structure (11a) is contacted with hydrogen gas and a catalytic amount of palladium black. The reactants are typically contacted in a suitable acidic medium such as acetic acid or methanolic hydrochloric acid. The reactants are typically shaken on a Parr hydrogenation apparatus at room tempeature for a period of time ranging from 2 hours to 10 days. The appropriate [4S-(4α,4aβ,5β,6α,7α,7aα)]-octahydro-1H-1-pyrindine-4,5,6,7-tetrol structure (12a) is recovered from the reaction zone by filtration and purified by ion exchange chromatography.

In step k₂, [4R-(4α,4aα,5α,6β,7β,7aβ)]-octahydro-5,6,7-tris(phenylmethoxy)-1H-1-pyrindin-4-ol of structure (10b) or the appropriate [4R-(4α,4aα,5α,6β,7β,7aβ)]-octahydro-1-alkyl-5,6,7-tris(phenylmethoxy)-1H-

1-pyrindin-4-ol of structure (11b) is deprotected to give the appropriate [4R-( 4α,4aα,5α,6β,7β,7aβ)]-octahydro-1H-1-pyrindine-4,5,6,7-tetrol of structure (12b) as described in step k₁.

Starting materials for use in Scheme A are readily available to one of ordinary skill in the art. For example, the preparation of methyl-2,3,4-tris(phenylmethoxy)-6-bromo-6-desoxy-α-D-mannopyranose and its conversion to 2,3,4-tris(phenylmethoxy)-5,6-dideoxy-D-lyxo-hex-5-enose (1) are described in Helv. Chim. Acta 62 2400 1979.

The following examples present typical syntheses as described in Scheme A. These examples are understood to be illustrative only and are not intented to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "μL" refers to microliters; "μg" refers to micrograms; and "μM" refers to micromolar.

EXAMPLE 1

[4R-(4α,4aα,5α,6β,7β,7aβ)]-Octahydro 1H-1-pyrindine-4,5,6,7-tetrol.hydrochloride—MDL-100,337A

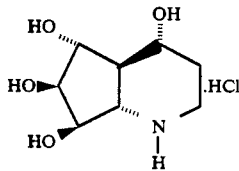

Step a:

[3aS-(3aα,4β,5α,6α,6aα)]-Hexahydro-1-[(4-methoxyphenyl)methyl]-4,5,6-tris(phenylmethoxy)-1H-cyclopent[c]isoxazole Dissolve freshly distilled 4-methoxybenzaldehyde (45.56 g, 334.6 mmol) in methanol (175 mL) and add hydroxylamine hydrochloride (30.06 g, 0.433 mol) and stir for 15 minutes. Add sodium methoxide (11.0 g, 0.204 mol) and stir at room temperature for 1 hour, partially concentrate in vacuo and add water (400 mL). Extract into ethyl ether (2×), wash with saturated sodium chloride and dry (MgSO₄). Evaporate the solvent in vacuo to give 4-methoxybenzyloxime as an off-white solid (49.95 g, 98.8%).

Dissolve 4-methoxybenzyloxime (1.49 g, 9.86 mmol) in acetic acid (15 mL) and add sodium cyanoborohydride (0.937 g, 14.9 mmol). Stir at room temperature for 15 minutes, basify with aqueous potassium hydroxide and extract into ethyl ether. Wash with water (2×), dry (MgSO₄) and evaporate the solvent in vacuo to give 4-methoxybenzylhydroxylamine as a white solid (0.724 g).

Mix methyl-2,3,4-tris(phenylmethoxy)-6-bromo-6-desoxy-α-D-mannopyranose (20.968 g, 39.75 mmol) and activated zinc dust (20.50 g, 314 mmol) in isopropanol (300 mL) and water (55 mL). Heat at reflux for 38 minutes, cool and filter. Rinse the zinc dust with a mixture of ethyl acetate/water, filter and dilute the filtrate with water. Extract with a mixture of ethyl acetate/cyclohexane (3×) and wash the combined organic extracts with water. Evaporate the solvent in vacuo to give 2,3,4-tris(phenylmethoxy)-5,6-dideoxy-D-lyxo-hex-5-enose.

Mix 2,3,4-tris(phenylmethoxy)-5,6-dideoxy-D-lyxo-hex-5-enose (39.75 mmol), 4-methoxybenzylhydroxylamine (7.368 g, 48.1 mmol) and methanol (250 mL). Heat at reflux for 16 hours, evaporate the solvent in vacuo and add aqueous potassium hydrogen carbonate. Extract with a mixture of ethyl acetate/cyclohexane (2×), wash the combined organic extracts with water and aqueous sodium chloride. Dry (MgSO₄), evaporate the solvent in vacuo and purify by silica gel chromatography (6:1 cyclohexane/ethyl acetate) to give the title compound as white crystals (16.4 g 74.8%); mp 59°-62° C.

IR (film from CHCl₃) $\nu_{max}$ 2872, 1514, 1454, 1250, 1136, 1118, 1028, 738, 698 cm⁻¹;

¹H NMR (CDCl₃) δ 7.35–7.15 (m, 17H), 6.89 (d, 2H, J=8.7 Hz), 4.73 (d, 1H, J=12.0 Hz), 4.57 (d, 1H, J=12.0 Hz), 4.55 (d, 1H, J=12.0 Hz), 4.52 (d, 1H, J=12.0 Hz), 4.38 (d, 1H, J=12.3 Hz), 4.26 (d, 1H, J=12.1 Hz), 4.28–4.17 (m, 2H), 3.97 (d, 1H, J=11.9 Hz), 3.95–3.86 (m, 2H), 3.80 (s, 3H), 3.66 (d, 1H, J=12.4 Hz), 3.65 (dd, 1H, J=5.0, 1.0 Hz), 3.47 (d, 1H, J=8.5 Hz), 3.25 (qd, 1H, J=8.0, 3.5 Hz);

MS (m/z) 580 (M⁺+29), 552 (M⁺+1,100), 444, 121; [α]$_D^{20}$ −64.9° (c 1.07, CHCl₃).

Anal. Calcd for C₃₅H₃₇NO₅: C, 76.20; H, 6.76; N, 2.54;

Found: C, 75.82; H, 6.89; N, 2.38.

Step b:

[1S-(1α,2α,3α,4β,5≠)]-[2-(Hydroxymethyl)-3,4,5-(phenylmethoxy)cyclopentyl][(4-methoxyphenyl)methyl]carbamic acid, 1,1-dimethylethyl ester Dissolve [3aS-(3aα,4β,5α,6α,6aα)]-hexahydro-1-[(4-methoxyphenyl)methyl]-4,5,6-tris(phenylmethoxy)-1H-cyclopent[c]isoxazole (4.24 g, 7.69 mmol) in 6:1 acetic acid/water (42 mL) and add activated zinc dust (1.80 g, 27.5 mmol). Heat at 50°-55° C. for 105 minutes. Evaporate the solvent in vacuo, dilute the residue with water and decant the clear aqueous layer from the residual zinc. Wash the zinc with water, aqueous potassium hydroxide and ethyl acetate. Combine all washings and decantates, separate the organic phase and extract the aqueous phase with a mixture of ethyl acetate/cyclohexane (2×). Wash the combined organic phases with aqueous potassium hydroxide, dilute ammonium hydroxide and aqueous sodium chloride. Dry (MgSO₄) and evaporate the solvent in vacuo to give [1S-(1α,2α,3α,4β,5β)]-[2-(hydroxymethyl)-3,4,5-(phenylmethoxy)cyclopentyl][(4-methoxyphenyl)methyl]amine.

Dissolve [1S-(1α,2α,3α,4β,5β)]-[2-(hydroxymethyl)-3,4,5-(phenylmethoxy)cyclopentyl][(4-methoxyphenyl)methyl]amine (7.69 mmol) in tetrahydrofuran (75 mL) and add di-tert-butyl dicarbonate (3.0 mL, 13 mmol). Heat at reflux overnight, add additional di-tert-butyl dicarbonate (0.75 mL) and heat at reflux for 3½ hours. Evaporate the solvent in vacuo and purify by silica gel chromatography (60/40 cyclohexane/ethyl acetate) to give the title compound as a viscous oil (4.711 g, 94%).

IR (film from CHCl₃) $\nu_{max}$ 3462, 2932, 1688, 1514, 1454, 1366, 1248, 1170, 1124, 1104, 1030, 752, 698 cm⁻¹;

¹H NMR (CDCl₃) δ 7.35–7.22 (m, 13H), 7.18–7.05 (m, 4H), 6.75 (d, 2H, J=8.3 Hz), 4.85–4.44 (m, 5H), 4.31–3.75 (m, 5H), 3.7–3.55 (m, 3H), 3.68 (s, 3H), 2.85–2.7 (bm, 2H), 1.48 (bs, 1H), 1.42 and 1.40 (2s, 9H);

MS (m/z) 654 (M⁺+1), 554 (100), 121;

[α]$_D^{20}$ +45.0° (c 1.11, CHCl$_3$).

Anal. Calcd for C$_{40}$H$_{47}$NO$_7$: C, 73.48; H, 7.25; N, 2.14.

Found: C, 73.61; H, 7.50; N, 1.91.

Step c:
[1S-(1α,2α,3α,4β,5β)]-[2-Formyl-3,4,5-tris(phenylmethoxy)cyclopentyl][(4-methoxyphenyl)methyl]carbamic acid, 1,1-dimethylethyl ester Dissolve [1S-(1α,2α,3α,4β,5β)]-[2-(hydroxymethyl)-3,4,5-(phenylmethoxy)cyclopentyl][(4-methoxyphenyl)methyl]carbamic acid, 1,1-dimethylethyl ester (160.6 mg, 0.246 mmol) in methylene chloride (6 mL) and add Dess-Martin periodinane (207 mg, 0.488 mmol). Stir for 15 minutes, pour into a mixture or ethyl ether/water containing potassium hydrogen carbonate (2.61 g, 26 mmol) and sodium thiosulfate (1.2 g, 7.6 mmol). Stir until both layers become clear, separate the organic phase and wash with aqueous sodium chloride. Dry (MgSO$_4$) and evaporate the solvent in vacuo to give the title compound as a colorless oil (158 mg).

$^1$H NMR (CDCl$_3$) δ 9.77 and 9.62 (2s in 8:3 ratio, 1H), 7.4–7.2 (m, 13H), 7.19–7.10 (m, 4H), 6.80 (d, 2H), 4.63–3.9 (m, 12H), 3.74 (s, 3H), 3.14 (m, 1H), 1.44 (s, 9H).

Step d:
[1S-(1α,2β,3α,4β,5β)]-[2-Formyl-3,4,5-tris(phenylmethoxy)cyclopentyl][(4-methoxyphenyl)methyl]carbamic acid, 1,1-dimethylethyl ester Dissolve [1S-(1α,2α,3α,4β,5β)]-[2-formyl-3,4,5-tris(phenylmethoxy)cyclopentyl][(4-methoxyphenyl)methyl]carbamic acid, 1,1-dimethylethyl ester (2.7 g, 4.28 mmol) in methylene chloride (50 mL). Cool to −78° C., place under nitrogen atmosphere and add a solution of 1,8-diazabicyclo[5.4.0]undec-7-ene (0.195 ml, 1.30 mmol) in methylene chloride (0.3 mL). Stir for 2 hours, quench at −78° C. with acetic acid (100 μL, 1.75 mmol). Partition between ethyl ether and water, separate the organic phase, dry (MgSO$_4$) and evaporate the solvent in vacuo to give the title compound as a colorless oil (2.70 g, 99.6%).

$^1$H NMR (CDCl$_3$) δ 9.53 (bs, 1H), 7.39–7.19 (m, 15H, 7.14 (d, 2H, J=8.7 Hz), 6.77 (d, 2H, J-8.7 Hz, 4.74–3.75 (m, 12H), 3.73 (s, 3H), 3.0–2.7 (bm, 1H), 1.45 (s, 9H); MS (m/z) 652 (M$^+$ +1), 596, 552, 488, 444, 121, 91 (100).

Step e:
[1R,2S,3R,4S,5R]-2-[[(1,1-dimethylethoxy)carbonyl][(4-methoxyphenyl)methyl]amino]-β-hydroxy-3,4,5-tris(phenylmethoxy)cyclopentanepropanoic acid, ethyl ester Place lithium hexamethyldisilazide (9.90 mL of a 1.0M solution in tetrahydrofuran, 9.9 mmol) under a nitrogen atmosphere and cool to −78° C. Add, by dropwise addition, ethyl acetate (1.01 mL, 10.3 mmol) and stir for 15 minutes. Add, by dropwise addition, a solution of [1S-(1α,2β,3α,4β,5β)]-[2-formyl-3,4,5-tris(phenylmethoxy)cyclopentyl][(4-methoxyphenyl)methyl]carbamic acid, 1,1-dimethylethyl ester (2.70 g, 4.14 mmol) in anhydrous tetrahydrofuran (25 mL) and stir for 30 minutes at −78° C. Quench at −78° C. with acetic acid, dilute with a mixture of ethyl ether/water and separate the organic phase. Wash the organic phase with aqueous sodium chloride, dry (MgSO$_4$), evaporate the solvent in vacuo and purify by silica gel chromatography (77:23 cyclohexane/ethyl acetate) to give the title compound (2.396 g, 78.3%).

Anal. Calcd for C$_{44}$H$_{53}$NO$_9$: C, 71.43; H, 7.22; N, 1.89.

Found: C, 71.60: H, 7.36; N, 1.77.

Step f:
[1R,2S,3R,4S,5R]-2-[[(1,1-Dimethylethoxy]carbonyl]amino]-β-hydroxy-3,4,5-tris(phenylmethoxy)cyclopentanepropanoic acid, ethyl ester Dissolve [1R,2S,3R,4S,5R]-2-[[(1,1-dimethylethoxy)carbonyl][(4-methoxyphenyl)methyl]amino]-β-hydroxy-3,4,5-tris(phenylmethoxy)-cyclopentanepropanoic acid, ethyl ester (2.018 g, 2.73 mmol) in a 4:1 mixture of acetonitrile/water (75 mL) and cool to 0° C. with an ice bath. Add ceric ammonium nitrate (4.23 g, 7.72 mmol) and stir for 1 hour. Pour into a mixture of water/ethyl acetate containing sodium chloride, separate the organic phase, wash with dilute sodium hydrogen carbonate and aqueous sodium chloride. Dry (MgSO$_4$), evaporate the solvent in vacuo and subject to Kugelrohr distillation to remove p-methoxybenzaldehyde (94° C. @ high vacuum) to give the title compound remaining as a white solid which is recrystallized from cyclohexane.

$^1$H NMR (CDCl$_3$) δ 7.39–7.25 (m, 15H), 4.70–4.43 (m 7H) 4.2–3.96 (m, 5H), 3.85–3.72 (m, 2.5H), 3.58 (bs, 0.5H), 2.62–2.47 (m, 2H), 1.82–1.75 (m, 1H), 1.46 (s, 9H), 1.25 and 1.24 (2t, 3H, J=7.1 Hz);

MS (m/z) 620 (M$^+$ +1), 564, 548, 521, 520 (100), 91;

Exact Mass Calcd for C$_{36}$H$_{46}$NO$_8$: 620.3223;

Found: 620.3187.

Anal. Calcd for C$_{36}$H$_{45}$NO$_8$: C, 69.77; H, 7.32; N. 2.26.

Found: C, 69.52: H, 7.74: N, 2.15.

Step g:
[1R,2S,3R,4S,5R]-2-amino-β-hydroxy-3,4,5-tris(phenylmethoxy)cyclopentanepropanoic acid, ethyl ester Dissolve [1R,2S,3R,4S,5R]-2-[[(1,1-dimethylethoxy)carbonyl]amino]-β-hydroxy-3,4,5-tris(phenylmethoxy)-cyclopentanepropanoic acid, ethyl ester (160 mg, 0.258 mmol) in ethyl ether (20 mL) and cool to 0°–5° C. with an ice bath. Bubble hydrogen chloride gas into the solution for 25–30 minutes. Remove the ice bath and evaporate the ethyl ether to ½ volume with a stream of nitrogen. Add fresh ethyl ether and carefully add aqueous sodium hydrogen carbonate. Separate the organic phase and extract the aqeuous phase with ethyl acetate. Combine the organic phases, wash with aqueous sodium chloride, dry (MgSO$_4$) and evaporate the solvent in vacuo to give the title compound as a mixture of epimers (140 mg).

IR (KBr) $\nu_{max}$ 3406, 3358, 1716, 1454, 1366, 1354, 1284, 1188, 1146, 1116, 1096, 1072, 1052, 1028, 734, 694 cm$^{-1}$;

MS (m/z) 560 (M$^+$ +41), 548 (M$^+$ +29), 520 (M$^+$ +1, 100).

Anal Calcd for C$_{31}$H$_{37}$NO$_6$: C, 71.65; H, 7.18; N, 2.70.

Found: C, 71.58; H, 7.49; N, 2.59.

Step h:
[4aR,5R,6S,7R,7aS]-Octahydro-4-hydroxy-5,6,7-tris(phenylmethoxy)-2H-1-pyrindin-2-one Dissolve [1R,2S,3R,4S,5R]-2-amino-β-hydroxy-3,4,5-tris(phenylmethoxy)cyclopentanepropanoic acid, ethyl ester (140 mg, 0.269 mmol) in methanol (15 mL) and add a catalytic amount of sodium methoxide. Heat at reflux under a nitrogen atmosphere for 90 minutes, add additional sodium methoxide and continue heating at reflux for 2½ hours. Evaporate the solvent in vacuo and partition between ethyl ether and aqueous ammonium chloride. Separate the organic phase, wash with aqueuos sodium chloride, dry (MgSO$_4$) and evaporate the solvent in vacuo to give the title compound as a yellow oil which solidifies on standing (122 mg).

$^1$H NMR (CDCl$_3$) δ 7.4–7.28 (m, 15H), 5.94 and 5.84 (2s in 1:2 ratio, 1H), 4.73–4.51 (m, 5H), 4.45 (s, 0.7H, J=11.5 Hz), 4.44 (s, 0.3H, J-11.8 Hz), 4.23 (m, 0.3H), 4.06–3.88 (m, 3H), 3.82–3.73 (m, 1H), 3.45 (dd, 0.7H, J=11.6, 10.0 Hz), 2.85 (dd, 0.7H, J=17.8, 6.7 Hz), 2.57 (dd, 0.3H, J=18.5, 4.2 Hz), 2.46 (dd, 0.3H, J=18.6, 1.5 Hz), 2.37 (bs, 0.7H), 2.30 (dd, 0.7H, J=18.0, 9.3 Hz), 2.08 (bs, 0.3H), 1.80–1.64 (m, 1H).

Step i:
[4S-(4α,4aβ,5β,6α,7α,7aα)]-Octahydro-5,6,7-tris(-phenylmethoxy)-1H-1-pyrindin-4-ol of structure (10a) and
[4R-(4α,4aα,5α,6β,7β,7aβ)]-octahydro-5,6,7-tris(-phenylmethoxy)-1H-1-pyrindin-4-ol (10b)

Add [4aR,5R,6S,7R,7aS]-octahydro-4-hydroxy-5,6,7-tris(phenylmethoxy)-2H-1-pyrindin-2-one (884 mg, 1.87 mmol) to a solution of lithium aluminum hydride (2.5 mL of a 1M solution in tetrahydrofuran) and place under a nitrogen atmosphere. Heat at reflux for 2 hours, cool and pour into dilute aqueous sodium hydroxide. Extract with a mixture of ethyl ether/ethyl acetate (2×), wash with aqueous sodium chloride and dry (MgSO$_4$). Evaporate the solvent in vacuo to give a mixture of the title compounds as a colorless oil (790 mg, 92%).

Separate and purify by silica gel chromatography (8–10% methanol/ethyl acetate) to give:

4S isomer (more polar) (203 mg, 24%); mp 85.5°–91.5° C.

IR (KBr) ν$_{max}$ 3534, 2888, 1454, 1352, 1122, 1110, 1088, 1072, 1030, 740, 696 cm$^1$;

$^1$H NMR (CDCl$_3$) δ 7.39–7.25 (m, 15H), 4.67 (d, 1H, J=11.7 Hz), 4.62 (s, 2H), 4.60 (d, 1H, J=11.7 Hz), 4.53 (d, 1H, J=11.7 Hz), 4.48 (d, 1H, J=11.6 Hz), 4.15 (m, 1H), 3.96–3.91 (m, 2H), 3.71 (dd, 1H, J=9.9, 6.2 Hz), 3.11 (dd, 1H, J=12.0, 9.9 Hz), 2.92–2.74 (m, 2H), 2.06 (bs, 2H), 1.68–1.6 (m, 2H), 1.52 (m, 1H, J=12.0, 9.2, 2.2 Hz); MS (m/z) 500 (M$^+$+41), 488 (M$^+$+29), 460 (M$^+$+1, 100); [α]$_D^{20}$+83.7° (c 1.0, CHCl$_3$).

Anal. Calcd for C$_{29}$H$_{33}$NO$_4$: C, 75.79; H, 7.24; N, 3.05;
Found: C, 75.62; H, 7.34; N, 2.99.

4R isomer (less polar) (424 mg, 49%); mp 110°–12° C. (softens at 105° C.).

IR (KBr) ν$_{max}$ 3396, 2894, 1140, 1104, 1076, 1028, 740, 696 cm$^{-1}$;

$^1$H NMR (CDCl$_3$) δ7.37–7.25 (m, 15H), 4.68 (d, 1H, J=11.5 Hz), 4.66 (d, 1H, J=11.5 Hz), 4.59 (s, 2H), 4.56 (d, 2H, J=11.5 Hz), 3.95 (dd, 1H, J=6.9, 2.8 Hz), 3.87 (dd, 1H, J=9.0, 2.8 Hz), 3.81 (dd, 1H, J=9.6, 6.9 Hz), 3.54 (td, 1H, J=10.2, 4.6 Hz), 3.06 (ddd, 1H, J=12.2, 4.3, 2.2 Hz), 2.71 (dd, 1H, J=11.3, 9.9 Hz), 2.55 (td, 1H, J=12.5, 2.6 Hz), 2.39 (bs, 2H), 1.91 (m, 1H, J=12.7 Hz) 1.44–1.29 (m, 2H); MS (m/z) 500 (M$^+$+41), 488 (M$^+$+29), 460 (M$^+$+1, 100), 442, 352;
[α]$_D^°$+45.9° (c 1.03, CHCl$_3$).

Anal. Calcd for C$_{29}$H$_{33}$NO$_4$: C, 75.79; H, 7.24; N, 3.05.
Found: C, 75.53; H, 7.49; N, 2.90.

Step k$_2$:
[4R-(4α,4aα,5α,6β,7β,7aβ)]-Octahydro-1H-1-pyrindine-4,5,6,7-tetrol.hydrochloride Dissolve [4R-(4α,4aα,5α,6β,7β,7aβ)]-octahydro-5,6,7-tris(phenylmethoxy)-1H-1-pyrindin-4-ol (414 mg, 0.091 mmol) in acetic acid (10 mL) and add palladium black (77 mg). Shake in a Parr hydrogenation apparatus for 5 days. Filter through filter aid, rinse with acetic acid and water, and evaporate the solvent in vacuo to give an amber oil (289 mg). Purify by ion exchange chromatography ([AG 50W-X8 (Bio-Rad)](0.1N –0.5N hydrochloric acid) to give the title compound as a white foam (123 mg, 61%).

$^1$H NMR (D$_2$O) δ 4.19 (m, 1H), 3.96–3.86 (m, 3H), 3.57 (ddd, 1H, J=13.3, 4.8, 2.0 Hz), 3.09 (td, 1H, J=13.6, 3.4 Hz), 3.02 (dd, 1H, J=12.4, 9.7 Hz), 2.26–2.17 (m, 1H), 1.73–1.57 (m, 2H).

EXAMPLE 2

[4S-(4α,4aβ,5β,6α,7α,7aβ)]-Octahydro-1H-1-pyrindine-4,5,6,7-tetrol.hydrochloride—MDL-102,022A

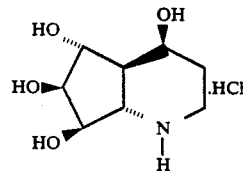

Dissolve [4S-(4α,4aβ,5β,6α,7α,7aα)]-octahydro-5,6,7-tris(phenylmethoxy)-1H-1-pyrindin-4-ol (173 mg, 0.376 mmol) in acetic acid (10 mL) and add palladium black (50 mg). Shake in a Parr hydrogenation apparatus for 4 days. Filter through filter aid, rinse with acetic acid and water, and evaporate the solvent in vacuo to give an amber oil (289 mg). Purify by ion exchange chromatography ([AG 50W-X8 (Bio-Rad)](water, 0.1N –0.5N hydrochloric acid) to give the title compound as a white crystalline solid (63 mg, 74%); mp 217°–219° C.

$^1$H NMR (D$_2$O) δ 4.31 (m, 1H, J=4.8 Hz), 4.15 (dd, 1H, J=9.2, 8.1 Hz), 3.95 (dd, 1H, J=7.9, 4.3 Hz), 3.84 (dd, 1H, J=10.0, 4.3 Hz), 3.40 (ddd, 1H, J=13.0, 4.9, 1.6 Hz), 3.28–3.17 (m, 2H), 2.11–2.01 (m, 1H), 1.96–1.74 (m, 3H).

EXAMPLE 3

[4R-(4α,4aα,5α,6β,7β,7aβ)]-Octahydro-1H-1-methyl-1-pyrindine-4,5,6,7-tetrol

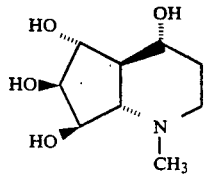

Optional Step j₂:
[4R-(4α,4aα,5α,6β,7β,7aβ)]-Octahydro-1-methyl-5,6,7-tris(phenylmethoxy)-1H-1-pyrindin-4-ol Dissolve [4R-(4α,4aα,5α,6β,7β,7aβ)]-octahydro-5,6,7-tris(phenylmethoxy)-1H-1-pyrindin-4-ol (2.30 g, 5 mmol) in methanol (distilled from Mg) (50 mL) and add formaldehyde (0.405 mL of a 37% solution in water, 5 mmol), sodium cyanoborohydride (0.62 g, 5 mmol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO₄) and evaporate the solvent in vacuo to give the title compound.

Step k₂:
[4R-(4α,4aα,5α,6β,7β,7aβ)]-Octahydro-1-methyl-1H-1-pyrindine-4,5,6,7-tetrol Dissolve [4R-(4α,4aα,5α,6β,7β,7aβ)]-octahydro-1-methyl-5,6,7-tris(phenylmethoxy)-1H-1-pyrindin-4-ol (43 mg, 0.091 mmol) in acetic acid (10 mL) and add palladium black (77 mg). Shake in a Parr hydrogenation apparatus for 5 days. Filter through filter aid, rinse with acetic acid and water, and evaporate the solvent in vacuo. Purify by ion exchange chromatography ([AG 50W-X8 (Bio-Rad)] to give the title compound.

EXAMPLE 4

[4R-(4α,4aα,5α,6β,7β,7aβ)]-Octahydro-1H-1-benzyl-1-pyrindine-4,5,6,7-tetrol

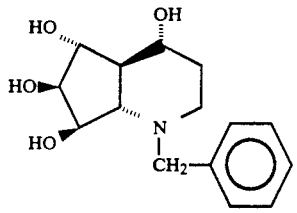

Optional Step j₂:
[4R-(4α,4aα,5α,6β,7β,7aβ)]-Octahydro-1-benzyl-5,6,7-tris(phenylmethoxy)-1H-1-pyrindin-4-ol Dissolve [4R-(4α,4aα,5α,6β,7β,7aβ)]-octahydro-5,6,7-tris(phenylmethoxy)-1H-1-pyrindin-4-ol (2.30 g, 5 mmol) in methanol (distilled from Mg) (50 mL) and add benzaldehyde (531 mg, 5 mmol), sodium cyanoborohydride (0.62 g, 5 mmol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO₄) and evaporate the solvent in vacuo to give the title compound.

Step k₂:
[4R-(4α,4aα,5α,6β,7β,7aβ)]-Octahydro-1H-1-benzyl-1-pyrindine-4,5,6,7-tetrol Dissolve [4R-(4α,4aα,5α,6β,7β,7aβ)]-octahydro-1-benzyl-5,6,7-tris(phenylmethoxy)-1H-1-pyrindin-4-ol (50 mg, 0.091 mmol) in acetic acid (10 mL) and add palladium black (77 mg). Shake in a Parr hydrogenation apparatus for 5 days. Filter through filter aid, rinse with acetic acid and water, and evaporate the solvent in vacuo. Purify by ion exchange chromatography ([AG 50W-X8 (Bio-Rad)] to give the title compound.

EXAMPLE 5

[4R-(4α,4aα,5α,6β,7β,7aβ)]-Octahydro-1H-1-(1,3-dihydroxyprop-2-yl)-1-pyrindine-4,5,6,7-tetrol

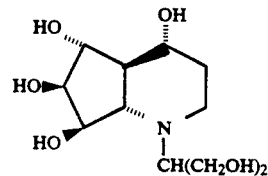

Optional Step j₂:
[4R-(4α,4aα,5α,6β,7β,7aβ)]-Octahydro-1-(1,3-dihydroxyprop-2-yl)-5,6,7-tris(phenylmethoxy)-1H-1-pyrindin-4-ol Dissolve [4R-(4α,4aα,5α,6β,7β,7aβ)]-octahydro-5,6,7-tris(phenylmethoxy)-1H-1-pyrindin-4-ol (1.22 g, 2.65 mmol) in methanol (17 mL) and add 1,3-dihydroxyacetone dimer (497 mg, 2.76 mmol) and sodium cyanoborohydride (202 g, 3.21 mmol). Stir at room temerature for 24 hours, evaporate the solvent in vacuo and partition the residue between aqueous potassium hydroxide (50 mL) and ethyl acetate (100 mL). Separate the organic phase, dry (MgSO₄), evaporate the solvent in vacuo and purify by silica gel chromatography to give the title compound Step k₂:
[4R-(4α,4aα,5α,6β,7β,7aβ)]-Octahydro-1H-1-(1,3-dihydroxyprop-2-yl)-1-pyrindine-4,5,6,7-tetrol Dissolve [4R-(4α,4aα,5α,6β,7β,7aβ)]-octahydro-1-(1,3-dihydroxyprop-2-yl)-5,6,7-tris(phenylmethoxy)-1H-1-pyrindin-4-ol (50 mg, 0.091 mmol) in acetic acid (10 mL) and add palladium black (77 mg). Shake in a Parr hydrogenation apparatus for 5 days. Filter through filter aid, rinse with acetic acid and water, and evaporate the solvent in vacuo. Purify by ion exchange chromatography ([AG 50W-X8 (Bio-Rad)] to give the title compound.

EXAMPLE 6

[4R-(4α,4aα,5α,6β,7β,7aβ)]-Octahydro-1H-1-(6-deoxy-1-O-methyl-mannosyl)-1-pyrindine-4,5,6,7-tetrol

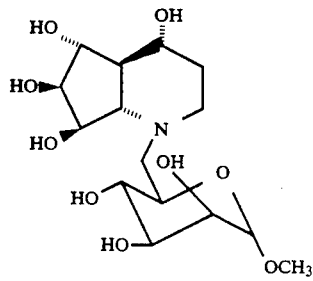

Optional Step j₂:
[4R-(4α,4aα,5α,6β,7β,7aβ)]-Octahydro-1-(6-deoxy-1-O-methyl-mannosyl)-5,6,7-tris(phenylmethoxy)-1H-1-pyrindin-4-ol Mix potassium carbonate (96.2 mg, 0.696 mmol), 6-bromo-6-deoxy-1-O-methyl-2,3,4-tris(phenylmethoxy)-mannose (264.3 mg, 0.501 mmol), [4R-(4α,4aα,5α,6β,7β,7aβ)]-octahydro-5,6,7-tris(phenylmethoxy)-1H-1-pyrindin-4-ol (229 mg, 0.498 mmol) and n-butanol (6 mL). Heat at reflux under a nitrogen atmosphere for 8 days. Cool, pour into a mixture of ethyl acetate/water and separate the organic phase. Wash the organic phase with aqueous sodium chloride, dry (MgSO₄) and evaporate the solvent in vacuo. Purify by silica gel chromatography to give the title compound.

Step k₂:
[4R-(4α,4aα,5α,6β,7β,7aβ)]-Octahydro-1H-1-(6-deoxy-1-O-methyl-mannosyl)-1-pyrindine-4,5,6,7-tetrol Dissolve [4R-(4α,4aα,5α,6β,7β,7aβ) octahydro-1-(6-deoxy-1-O-methyl-mannosyl)-5,6,7-tris(phenylmethoxy)-1H-1-pyrindin-4-ol (82 mg, 0.091 mmol) in acetic acid (10 mL) and add palladium black (77 mg) Shake in a Parr hydrogenation apparatus for 5 days. Filter through filter aid, rinse with acetic acid and water, and evaporate the solvent in vacuo. Purify by ion exchange chromatography ([AG 50W-X8 (Bio-Rad)]) to give the title compound.

The compounds of this invention are alpha-mannosidase inhibitors, immunomodulatory agents, chemoprotective agents, radioprotective agents and antimetastatic agents.

In practicing the method of this invention, an effective amount of a compound of this invention is that amount required to inhibit Mannosidase II and thus to elicit a chemo- or radioprotective, immunostimulatory, or antimetastatic effect. Immunostimulatory agents are desirable in those instances where the immune system of the patient has been compromised, such as in those patients infected with HIV, the causative agent in AIDS and ARC, as well as patients undergoing bone marrow transplants and in patients having various cancers. The compounds of this invention can also be used to prevent or to treat metastasis of tumors. In addition, the compounds of this invention can be used as chemo- and radioprotective agents by virtue of the ability of these compounds to reduce myelosuppression with resultant leukopenia and by virtue of the compounds to stimulate hematopoietic activity.

The specific dosage for the treatment of any specific patient in need of chemoprotective, radioprotective, immunostimulant or antimetastatic therapy will depend upon such factors as size, type, and age of the patient as well as the severity of the disease state, all of which are factors normally familar to and considered by the attending diagnostitian treating the patient. Generally, the compounds are to be administered orally at a dose of from 0.2 to 20 mg/kg of patient body weight per day, with a dose of from 0.5 to 5 mg/kg being preferred. The compounds preferably are to be administered orally at mealtimes in single or multiple unit doses containing from 25 mg to 250 mg of the chosen compound.

In practicing the method of this invention, the active ingredient is preferably incorporated in a composition comprising a pharmaceutical carrier and from about 5 to about 90 percent by weight of a compound of the invention or a pharmaceutically-acceptable salt thereof.

The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral. For oral administration the formula 1 compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula 1 compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethyleneglycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula 1 compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

What is claimed is:

1. A compound of the formula

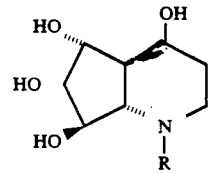

wherein R is a hydrogen, a (C$_1$–C$_6$)alkyl optionally substituted with one or two hydroxy groups, a glycosyl group, or a group of the formula —(CH$_2$)$_n$—Ar wherein n is an integer of from 1 to 4 and Ar is a phenyl group optionally substituted with one or two groups selected from the group consisting of (C$_1$–C$_4$)alkyl, (C$_1$–C$_4$)alkoxy, F, Cl, Br, I, amino, mono(C$_1$–C$_4$)alkylamino, or di(C$_1$–C$_4$)alkylamino, or a pharmaceutically acceptable salt thereof.

2. A compound of claim 1 wherein R is a hydrogen, methyl, 1,3-dihydroxyprop-2-yl, benzyl or mannosyl group.

3. A compound of claim 1 wherein the 4-hydroxy group is of the alpha-configuration.

4. A compound of claim 2 wherein the 4-hydroxy group is of the beta-configuration.

5. A pharmaceutical composition comprising a compound of claim 1 together with pharmaceutical carriers.

6. A composition comprising a compound of claim 1 and a carrier.

7. A compound according to claim 1 wherein the compound is [4R-(4α,4aα,5α,6β,7β,7aβ)]-octahydro-1H-1-pyrindine-4,5,6,7-tetrol.

8. A compound according to claim 1 wherein the compound is 4S-(4α,4aβ,5β,6α,7α,7aα)]-octahydro-1H-1-pyrindine-4,5,6,7-tetrol.

* * * * *

UNITED STATES PATENT AND TRADEMARK OFFICE
CERTIFICATE OF CORRECTION

PATENT NO. : 5,262,425      Page 1 of 8

DATED : November 16, 1993

INVENTOR(S) : Robert A. Farr, Mohinder S. Kang, Norton, P. Peet, Sai P. Sunkara

It is certified that error appears in the above-identified patent and that said Letters Patent is hereby corrected as shown below:

At Column 1, lines 53-59, the patent reads

"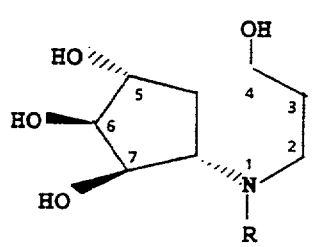"  1 and should read

--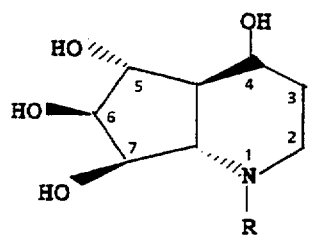--  1

UNITED STATES PATENT AND TRADEMARK OFFICE
CERTIFICATE OF CORRECTION

PATENT NO. : 5,262,425

DATED : November 16, 1993

INVENTOR(S) : Robert A. Farr, Mohinder S. Kang, Norton, P. Peet, Sai P. Sunkara

It is certified that error appears in the above-identified patent and that said Letters Patent is hereby corrected as shown below:

At Column 3, line 1, the patent reads "whererin" and should read -- wherein --.

At Column 3 lines 45 through Column 4 lines 40, the patent reads "                                                                 "

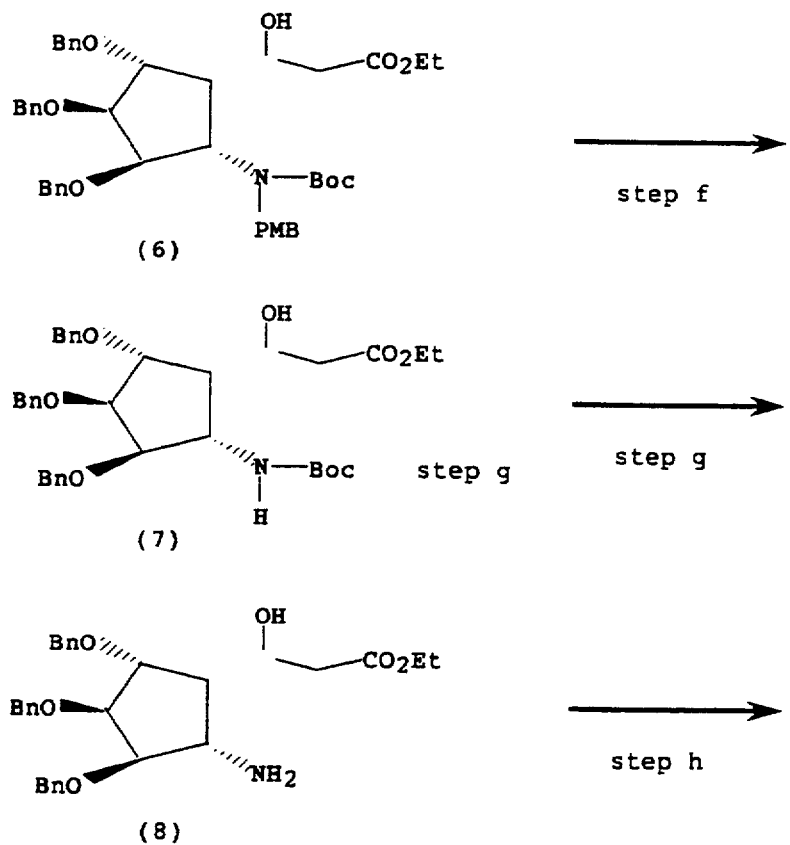

UNITED STATES PATENT AND TRADEMARK OFFICE
CERTIFICATE OF CORRECTION

PATENT NO. : 5,262,425  Page 3 of 8
DATED : November 16, 1993
INVENTOR(S) : Robert A. Farr, Mohinder S. Kang, Norton, P. Peet, Sai P. Sunkara It is certified that error appears in the above-identified patent and that said Letters Patent is hereby corrected as shown below:

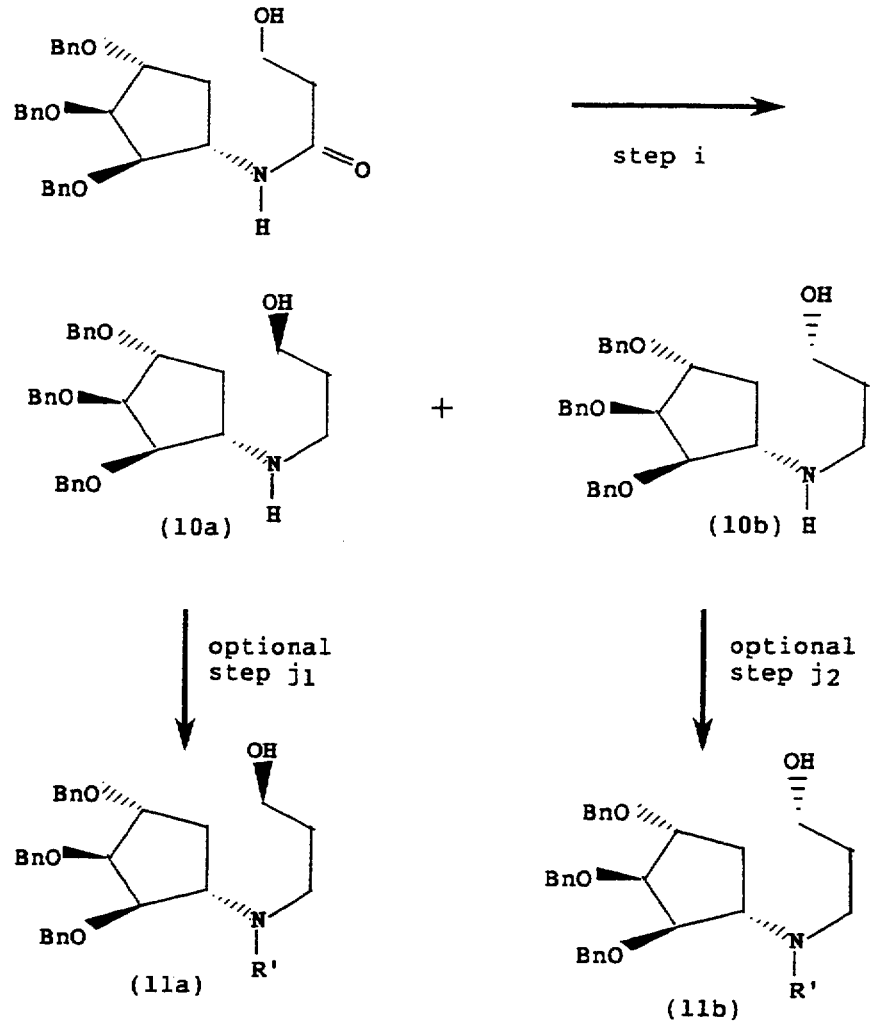

UNITED STATES PATENT AND TRADEMARK OFFICE
CERTIFICATE OF CORRECTION

PATENT NO. : 5,262,425        Page 4 of 8
DATED     : November 16, 1993
INVENTOR(S) : Robert A. Farr, Mohinder S. Kang, Norton, P. Peet, Sai P. Sunkara It is certified that error appears in the above-identified patent and that said Letters Patent is hereby corrected as shown below:

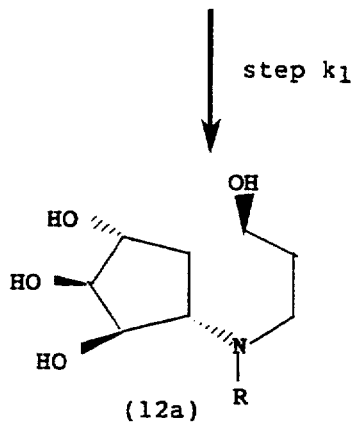 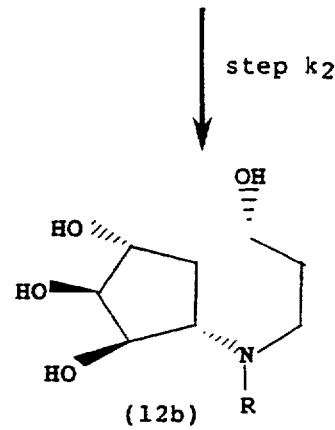

" R' = other than hydrogen "

and should read

-- 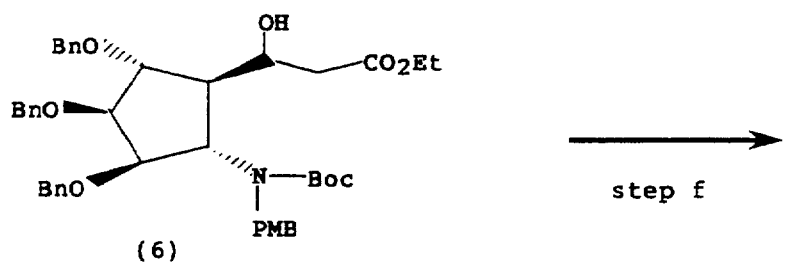 --

UNITED STATES PATENT AND TRADEMARK OFFICE
CERTIFICATE OF CORRECTION

PATENT NO. : 5,262,425

DATED : November 16, 1993

INVENTOR(S) : Robert A. Farr, Mohinder S. Kang, Norton, P. Peet, Sai P. Sunkara

It is certified that error appears in the above-identified patent and that said Letters Patent is hereby corrected as shown below:

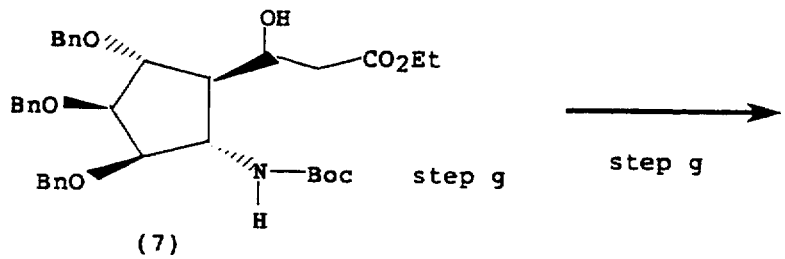

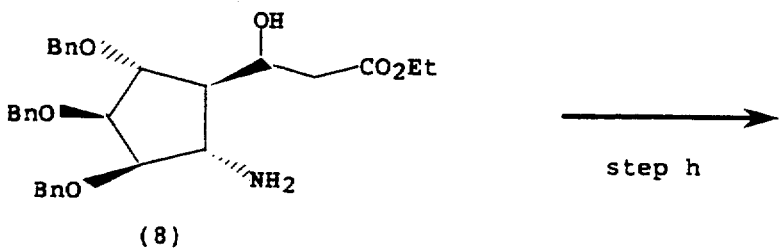

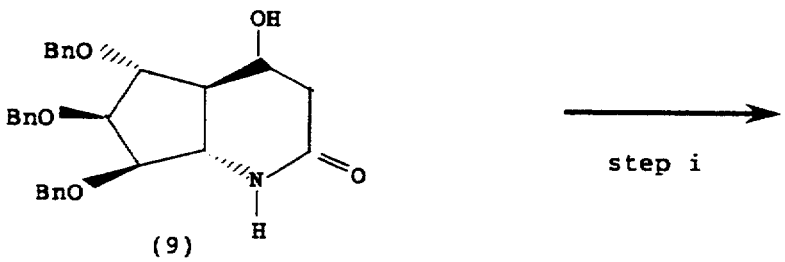

UNITED STATES PATENT AND TRADEMARK OFFICE
CERTIFICATE OF CORRECTION

PATENT NO. : 5,262,425

DATED : November 16, 1993

INVENTOR(S) : Robert A. Farr, Mohinder S. Kang, Norton. P. Peet, Sai P. Sunkara

It is certified that error appears in the above-identified patent and that said Letters Patent is hereby corrected as shown below:

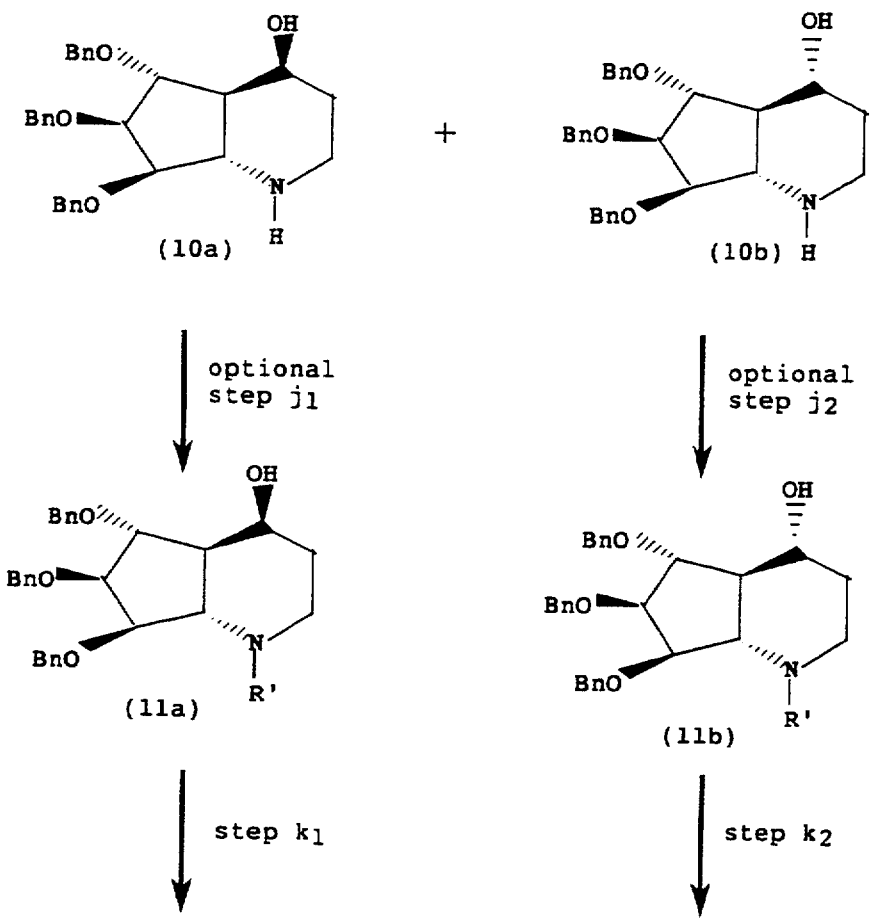

UNITED STATES PATENT AND TRADEMARK OFFICE
CERTIFICATE OF CORRECTION

PATENT NO. : 5,262,425
DATED : November 16, 1993
INVENTOR(S) : Robert A. Farr, Mohinder S. Kang, Norton, P. Peet, Sai P. Sunkara It is certified that error appears in the above-identified patent and that said Letters Patent is hereby corrected as shown below:

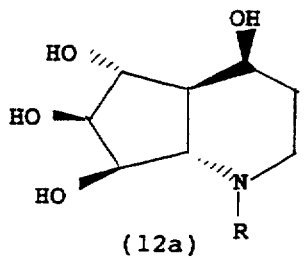 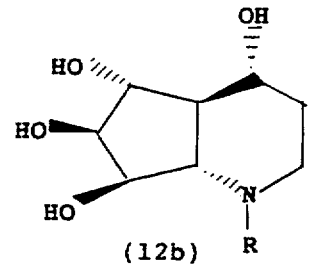

R' = other than hydrogen

At Column 4, line 51, the patent reads "an slight" and should read -- a slight --.

At Column 6, line 19, the patent reads "5β)]-[2-tris" and should read -- 5β)]-[2-formyl-3,4,5-tris --.

At Column 7, line 46, the patent reads "β-3,4,5-" and should read -- β-hydroxy-3,4,5- --.

At Column 7, line 65, the patent reads "7aβ)" and should read -- 7aα) --.

At Column 8, line 60, the patent reads "tempeature", and should read -- temperature --.

At Column 9, line 14, the patent reads "intented", and should read -- intended --.

At Column 10, line 31, the patent reads "5 )]" and should read -- 5β)]) --.

At Column 11, line 44, the patent reads "15H," and should read -- 15H), --.

UNITED STATES PATENT AND TRADEMARK OFFICE
CERTIFICATE OF CORRECTION

PATENT NO. : 5,262,425

DATED : November 16, 1993

INVENTOR(S) : Robert A. Farr, Mohinder S. Kang, Norton, P. Peet, Sai P. Sunkara

It is certified that error appears in the above-identified patent and that said Letters Patent is hereby corrected as shown below:

At Column 13, line 8, the patent reads "aqueuos", and should read -- aqueous --.

At Column 13, line 68, the patent reads "$[\alpha]_D$" and should read -- $[\alpha]_D^{20}$ --.

At Column 14, line 26, the patent reads "7aβ)" and should read -- 7aα) --

At Column 20, lines 20-28, the patent reads

"
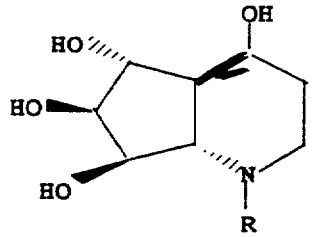
"

and should read

--
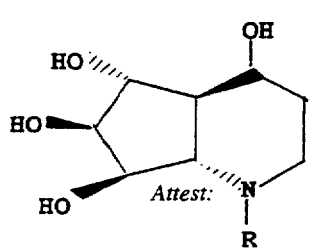
--

Signed and Sealed this

Ninth Day of August, 1994

BRUCE LEHMAN

*Attesting Officer*   Commissioner of Patents and Trademarks